United States Patent
Fish et al.

(10) Patent No.: US 11,845,721 B2
(45) Date of Patent: Dec. 19, 2023

(54) PROCESSES AND SYSTEMS FOR SEPARATING CARBON DIOXIDE IN THE PRODUCTION OF ALKANES

(71) Applicant: Dow Global Technologies LLC, Midland, MI (US)

(72) Inventors: Barry Brent Fish, Freeport, TX (US); Peter E. Groenendijk, Terneuzen (NL); Andrzej Malek, Midland, MI (US); Davy L. S. Nieskens, Terneuzen (NL); Brien A. Stears, Friendswood, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 17/830,038

(22) Filed: Jun. 1, 2022

(65) Prior Publication Data

US 2022/0289647 A1    Sep. 15, 2022

Related U.S. Application Data

(62) Division of application No. 16/607,780, filed as application No. PCT/US2018/029390 on Apr. 25, 2018, now Pat. No. 11,377,403.

(Continued)

(51) Int. Cl.
| | |
|---|---|
| *B01D 3/14* | (2006.01) |
| *C07C 7/08* | (2006.01) |
| *B01D 3/40* | (2006.01) |
| *B01D 53/14* | (2006.01) |

(52) U.S. Cl.
CPC ............... *C07C 7/08* (2013.01); *B01D 3/143* (2013.01); *B01D 3/40* (2013.01); *B01D 53/1418* (2013.01);

(Continued)

(58) Field of Classification Search
CPC ...... B01D 3/143; B01D 3/40; B01D 53/1418; B01D 53/1425; B01D 53/1475; B01D 2252/204; C07C 7/08
See application file for complete search history.

(56) References Cited

U.S. PATENT DOCUMENTS

| 2,613,132 A | 10/1952 | Hutchinson |
| 4,350,511 A | 9/1982 | Holmes et al. |

(Continued)

FOREIGN PATENT DOCUMENTS

| CN | 102559270 A | 7/2012 |
| EP | 352870 A1 | 1/1990 |

OTHER PUBLICATIONS

Brazil Technical Report issued by the Brazilian Patent Office for Patent Application No. BR112019020774-0 dated Jun. 22, 2022 (4 pages).

(Continued)

*Primary Examiner* — Jonathan Miller
(74) *Attorney, Agent, or Firm* — Dinsmore & Shohl LLP (57) ABSTRACT

A method for separating $CO_2$ from $C_2$ to $C_5$ alkanes includes introducing a first stream including $C_2$ to $C_5$ alkanes and $CO_2$ into a first separation zone, the first separation zone including a hydrocarbon solvent, and separating the first stream into a recycle stream and a second stream in the first separation zone. The recycle stream including $CO_2$ and one or more of CO, $H_2$, and $CH_4$, and the second stream including $C_2$ to $C_5$ alkanes. The method further includes introducing the second stream into a second separation zone, and separating the second stream into a third stream and a fourth stream, wherein the third stream includes $C_2$ alkanes and the fourth stream includes $C_3$ to $C_5$ alkanes.

12 Claims, 3 Drawing Sheets

Related U.S. Application Data (60) Provisional application No. 62/491,663, filed on Apr. 28, 2017.

(52) U.S. Cl.
CPC ..... *B01D 53/1425* (2013.01); *B01D 53/1475* (2013.01); *B01D 2252/204* (2013.01)

(56) References Cited

U.S. PATENT DOCUMENTS

| | | | |
|---|---|---|---|
| 4,383,842 A | 5/1983 | O'Brien | |
| 4,428,759 A | 1/1984 | Ryan et al. | |
| 4,462,814 A | 7/1984 | Holmes et al. | |
| 4,654,062 A | 3/1987 | Gottier | |
| 11,377,403 B2 * | 7/2022 | Fish | B01D 3/146 |
| 2012/0063978 A1 * | 3/2012 | Baugh | B01D 53/1493 |
| | | | 423/228 |
| 2015/0322350 A1 | 11/2015 | Iyer et al. | |

OTHER PUBLICATIONS

Damasceno, Arthur Siqueira et al., "Evaluation of Control Properties of an Extractive Distillation System in the Separation of CO2 and Ethane—Conventional Sequence: With and Without Thermal Integration", Proceedings of the Brazilian Congress of Chemical Engineering, Sep. 25, 2009 (10 total pages with English Abstract).

Argentina Report Previous to Final Decision for Patent Application No. 20180101070 dated Jul. 25, 2022 English translation—4 total pages.

Hong et al., "To Break an Azeotrope: The Use of n-Pentane to Break the CO2-Ethane Azeotrope, for CO2 EOR Gas Processing", Ind. Eng. Chem. Process Des. Dev., 1986, 25, 736-741.

Lastari et al., "Extractive distillation for CO2-ethane azeotrope separation", Chemical Engineering and Processing, 2012, 52, 155-161.

Ebrahimzadeh et al., "Alternative extractive distillation system for CO2-ethane azeotrope separation in enhanced oil recovery processes", Applied Thermal Engineering, 2016, 96,39-47.

International Search Report and Written Opinion pertaining to PCT/US2018/029390, dated Jun. 27, 2018.

Examination Report pertaining to corresponding G.C.C. Patent Application No. 2018-35201 dated Feb. 2, 2020.

Notice of Allowance pertaining to U.S. Appl. No. 16/607,780 dated Mar. 8, 2022 (8 pgs).

* cited by examiner

PROCESSES AND SYSTEMS FOR SEPARATING CARBON DIOXIDE IN THE PRODUCTION OF ALKANES

CROSS REFERENCE TO RELATED APPLICATION

This application is a divisional application of U.S. patent application Ser. No. 16/607,780, filed on Oct. 24, 2019, entitled PROCESSES AND SYSTEMS FOR SEPARATING CARBON DIOXIDE IN THE PRODUCTION OF ALKALINES, the entire disclosure of which is hereby incorporated by reference.

BACKGROUND

Field

The present specification generally relates to processes and systems for separating carbon dioxide ($CO_2$) in the production of alkanes and, more specifically, is directed to processes and systems that separate $CO_2$ from a product stream comprising alkanes using a hydrocarbon solvent.

Technical Background

In various processes—such as, for example, a process for forming light alkanes (e.g., $C_2$ to $C_5$ alkanes) using a hybrid catalyst—hydrocarbon-derived gas streams, such as, for example, syngas, are converted to light alkanes, $CO_2$, and methane ($CH_4$). In a hybrid process, alkanes are formed by carbon monoxide hydrogenation to hydrocarbons, potentially via a methanol intermediate. The $CO_2$ is generally formed by a traditional water gas shift reaction. The product stream in these processes may also contain unreacted hydrogen ($H_2$) and carbon monoxide (CO), which are desirably recycled back to the reactor that forms the light alkanes from the hydrogen-containing gas stream to achieve a highly efficient system that does not unnecessarily waste raw materials.

In the above-described processes, $CO_2$ may be recycled back to the reactor that forms the light alkanes from the hydrogen-containing gas stream, or it is purged from the system. However, separating the $CO_2$ from the light alkane products can be challenging. Although conventional systems for separating light alkanes from $CO_2$ exist, they can be costly, inefficient, and may utilize undesirable chemicals.

Accordingly, a need exists for processes and systems that can efficiently separate light alkane products and $CO_2$.

SUMMARY

According to one embodiment, a method for separating $CO_2$ from $C_2$ to $C_5$ alkanes, comprises: introducing a first stream comprising $C_2$ to $C_5$ alkanes and $CO_2$ into a first separation zone, the first separation zone comprising a hydrocarbon solvent; separating the first stream into a recycle stream and a second stream in the first separation zone, wherein the recycle stream comprises $CO_2$ and one or more of CO, $H_2$, and $CH_4$, and the second stream comprises $C_2$ to $C_5$ alkanes; introducing the second stream into a second separation zone; and separating the second stream into a third stream and a fourth stream, wherein the third stream comprises $C_2$ alkanes and the fourth stream comprises $C_3$ to $C_5$ alkanes.

In another embodiment, a system for separating $CO_2$ from $C_2$ to $C_5$ alkanes, comprises: a first separation zone comprising a hydrocarbon solvent and that is configured to separate a first stream comprising $C_2$ to $C_5$ alkanes and $CO_2$ into a recycle stream and a second stream, wherein the recycle stream comprises $CO_2$ and one or more of CO, $H_2$, and $CH_4$, and the second stream comprises $C_2$ to $C_5$ alkanes; and a second separation zone that is fluidly connected to the first separation zone and that is configured to separate the second stream into a third stream and a fourth stream, wherein the third stream comprises $C_2$ alkanes and the fourth stream comprises $C_3$ to $C_5$ alkanes.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Reference will now be made in detail to embodiments of processes and systems for separating $CO_2$ in the production of alkanes. Whenever possible, the same reference numerals will be used throughout the drawings to refer to the same or like parts. In one embodiment, A method for separating $CO_2$ from $C_2$ to $C_5$ alkanes includes introducing a first stream including $C_2$ to $C_5$ alkanes and $CO_2$ into a first separation zone, the first separation zone including a hydrocarbon solvent, and separating the first stream into a recycle stream and a second stream in the first separation zone. The recycle stream including $CO_2$ and one or more of CO, $H_2$, and $CH_4$, and the second stream including $C_2$ to $C_5$ alkanes. The method further includes introducing the second stream into a second separation zone, and separating the second stream into a third stream and a fourth stream, wherein the third stream includes $C_2$ alkanes and the fourth stream includes $C_3$ to $C_5$ alkanes. The third stream comprises $C_2$ alkanes, and the fourth stream comprises $C_3$ to $C_5$ alkanes. In another embodiment, a system for separating $CO_2$ from $C_2$ to $C_5$ alkanes includes a first separation zone comprising a hydrocarbon solvent and that is configured to separate a first stream comprising $C_2$ to $C_5$ alkanes and $CO_2$ into a recycle stream and a second stream, and a second separation zone, which is fluidly connected to the first separation zone, and that is configured to separate the second stream into a third stream and a fourth stream. The recycle stream includes $CO_2$ and one or more of CO, $H_2$, and $CH_4$, and the second stream includes $C_2$ to $C_5$ alkanes. The third stream includes $C_2$ alkanes and the fourth stream includes $C_3$ to $C_5$ alkanes.

As used herein, the term "light alkanes" refers to $C_2$ to $C_5$ alkanes, including, but not limited to, ethane, propane, n-butane, isobutane, pentane, isopentane, and neopentane.

The scheme used to separate and control the recycle streams, including separation of the $CO_2$ in the various streams, will impact reactor composition, reactor flow, CO conversion, $CO_2$ production or conversion across the reactor, and reactor productivity. Conventional methods for removing $CO_2$ from a gas stream include using polar solvents to trap $CO_2$, but leave the other light gases in the gas stream. Such methods include: using methanol as a solvent (e.g., Rectisol® process); using di-methyl ethers of polyethylene glycol (e.g., Selexol™ process); using amine components, such as, for example, monoethanlamine (MEA), diethanolamine (DEA), or methyl diethanolamine (MDEA), in water (e.g., Ucarsol™ process); using potassium carbonate in water (e.g., Benfield™ process); and using caustic wash systems. However, in each of these systems $CO_2$ is the main constituent of the product stream, and the $CO_2$ is removed from the product stream before other components are separated. The $CO_2$ that has been removed is generally purged from the system in conventional $CO_2$ separation systems.

Figure 1:
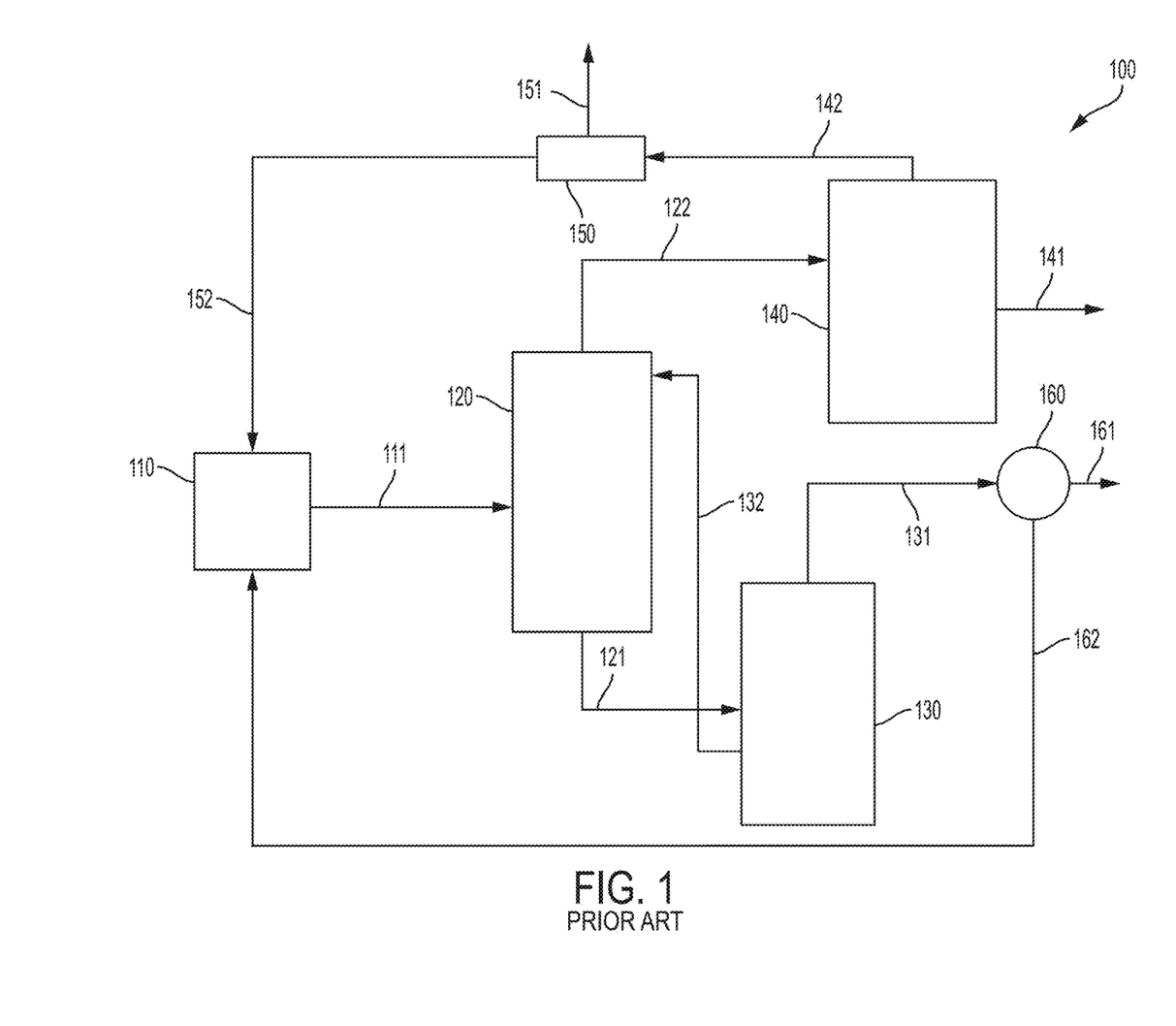
FIG. 1 schematically depicts a conventional system for separating $CO_2$ in the production of alkanes.

With reference now to FIG. 1, a conventional $CO_2$ separation system 100, such as a system for using one of the above-described processes, will be described. A reaction zone 110 converts a gas stream (not shown) into a feed stream 111 comprising light alkanes and $CO_2$. In embodiments, the feed stream 111 also comprises one or more of CO, $H_2$, and methane. The reactions that occur in the reaction zone 110 are not limited and may be any conventional reactions that form the desired light alkanes and $CO_2$ as a byproduct. Such reactions include, for example, the conversion of syngas to light alkanes using a hybrid catalyst in a reactor. In some embodiments, the hybrid catalyst comprises a methanol synthesis component and a solid microporous acid component. In other embodiments, different conventional reactions may be used to form light alkanes and $CO_2$ as a byproduct. It should be understood that, in embodiments, the reaction zone 110 may include any number of reactors. For instance, in some embodiments, the reaction zone 110 may comprise a first reactor for converting raw gases—such as, for example, methane or natural gas—into syngas, and the reaction zone 110 may comprise a second reactor—such as, for example, a reactor containing the above-described hybrid catalyst—for converting the syngas into light alkanes and a $CO_2$ byproduct. Accordingly, in one or more embodiments, the reaction zone 110 includes any necessary reactors for converting raw gas streams into feed stream 111 that comprises light alkanes and $CO_2$.

The feed stream 111 is sent from the reaction zone 110 to a $CO_2$ scrubber 120 that is fluidly connected to the reaction zone 110, a demethanizer 140, and a stripper 130. The $CO_2$ scrubber 120 comprises a solvent that isolates $CO_2$ from the other components of the feed stream 111—such as, for example, light alkanes and, optionally, one or more of CO, $H_2$, and $CH_4$. Any conventional solvent for isolating $CO_2$ may be used. For example, the solvent may comprise one or more of methanol, di-methyl ethers of polyethylene glycol, an aqueous solution comprising amine components (such as, for example, MEA, DEA, or MDEA), or an aqueous solution comprising potassium carbonate. Once the $CO_2$ has been isolated from the other components of the feed stream 111, the $CO_2$ exits the scrubber 120 as $CO_2$ solvent stream 121 that comprises $CO_2$ and the solvent described above. The $CO_2$ solvent stream 121 is sent to a stripper 130 that is fluidly connected to the scrubber 120. Similarly, the other components of the feed stream 111 that have been isolated from $CO_2$ (such as, for example, light alkanes and, optionally, one or more of CO, $H_2$, and $CH_4$) exit the scrubber 120 as a first product stream 122. The first product stream 122 is sent from the scrubber 120 to a demethanizer 140. It should be understood that any conventional scrubber suitable for scrubbing $CO_2$ from the feed stream 111 may be used as the scrubber 120.

The demethanizer 140 is fluidly connected to the scrubber 120 and the reaction zone 110. An optional first splitter 150 may be positioned between, and fluidly connected to, the demethanizer 140 and the reaction zone 110. At the demethanizer 140, the first product stream 122 is separated into a final product stream 141 that comprises light alkanes and a recycle stream 142 that comprises one or more of $H_2$, CO, and $CH_4$. Any conventional type of demethanizer that is capable of separating light alkanes from other components in the first product stream 122 may be used as the demethanizer 140. The final product stream 141 exits the conventional $CO_2$ separation system and may be used in various chemical processes. The recycle stream 142 is sent from the demethanizer 140 to the reaction zone 110 where the components of the recycle stream 142 can be used as reactants in the reaction zone 110. In embodiments, the demethanizer 140 is operated at a temperature of from −80° C. to −60° C., such as about −70° C., and at a pressure from 25 bar (2500 kPa) to 35 bar (3500 kPa), such as about 30 bar (3000 kPa).

In some embodiments, the recycle stream 142 may comprise inert gases, such as, for example, nitrogen or argon, which, in some embodiments, may be present in the feed stream 111. In such embodiments, an optional first splitter 150 may be fluidly connected to the demethanizer 140 and the first reaction zone 110 such that the recycle stream 142 passes through the first splitter 150. At the first splitter 150, a portion of the recycle stream 142 is removed from the conventional $CO_2$ separation system 100 as an inert gas containing stream 151. The remainder of the recycle stream 142 exits the first splitter 150 as a second recycle stream 152 and is sent to the reaction zone 110. In embodiments, a portion of the recycle stream 142 is withdrawn from the process to prevent inert build-up and the remaining portion of stream 142 is sent directly from the demethanizer 140 to the reaction zone 110. In one or more embodiments, the recycle stream 142, the inert gas containing stream 151, and the second recycle stream 150 have the same composition. It should be understood that any conventional device that can separate gas stream 142 into two streams and regulate the flow of gaseous stream 142 in each of the two streams may be used as the first splitter 150.

As stated above, the $CO_2$ solvent stream 121 is sent from the scrubber 120 to the stripper 130. The stripper 130 is fluidly connected to the scrubber 120 and a second splitter 160. At the stripper 130 the $CO_2$ solvent stream 121 is stripped to form a lean solvent and gaseous $CO_2$. This stripping of the $CO_2$ solvent stream 121 can be conducted by any conventional method, and is not limited herein. The solvent that remains after the $CO_2$ has been stripped therefrom exits the stripper 130 as a solvent stream 132 and is returned to the scrubber 120 where it can again be used as a solvent to separate $CO_2$ from the feed stream 111. Similarly, the gaseous $CO_2$ that has been stripped from the $CO_2$ solvent stream 121 exits the stripper 130 as $CO_2$ stream 131 and is sent to a second splitter 160 that is fluidly connected to the stripper 130. It should be understood that any conventional stripper suitable for stripping $CO_2$ from the type of solvent used in the conventional $CO_2$ separation system 100 may be used as the stripper 130. Conventionally $CO_2$ separation from the solvent is achieved by adding energy to the process. This means adding heat or energy to the process stream. At higher temperatures, part of the solvent may also evaporate, but it can be recovered using condensation at low temperature. In embodiments, process heat, such as steam, and cooling, such as cooling water, are used for this process.

The second splitter 160 is fluidly connected to the stripper 130 and the reaction zone 110. At the second splitter 160 the gaseous $CO_2$ stream is split into a $CO_2$ purge stream 161 that exits the conventional $CO_2$ separation system 100 and a $CO_2$ recycle stream 162 that is sent back to the reaction zone 110. It should be understood that the amount $CO_2$ that is purged from the conventional $CO_2$ separation system 100 as $CO_2$ purge stream 161 and the amount of $CO_2$ that is sent back to the reaction zone 110 is not limited and will be determined base on the need for $CO_2$ at the reaction zone 110. It should be understood that any conventional device that can separate gaseous $CO_2$ into two streams and regulate the flow of gaseous $CO_2$ in each of the two streams may be used as the second splitter 160.

The above method provides for recycling $CO_2$ (such as by $CO_2$ recycle stream 162) to be used in the reaction zone 110. However, there are inefficiencies with conventional $CO_2$ separation systems, such as the one described above. One inefficiency is that a large amount of $CO_2$ must be removed. For instance, in many systems the mass ratio of $CO_2$ to alkane at the outlet of the reaction zone 110 is greater than one. When the $CO_2$ to alkane ratio is greater than one, more than one pound of $CO_2$ must be removed for every pound of alkanes, which requires a large amount of energy per pound of alkane produced. Another inefficiency of the conventional $CO_2$ separation systems, such as those described above, is that the $CO_2$ recycle stream 162 that exits the stripper 130 and is sent back to the reaction zone 110 is at a low pressure, so it needs to be compressed before it can be used in the reaction zone 110, which requires additional capital investment and energy.

In view of the above inefficiencies of conventional $CO_2$ separation systems, it is desirable to separate $H_2$, CO, $CO_2$, and $CH_4$ into one stream and light alkanes into another stream. This separation scheme is not easily achieved because ethane (i.e., $C_2$ alkane) and $CO_2$ have an azeotrope and cannot be separated by simple distillation. However, systems and methods for separating $CO_2$ during the preparation of alkanes according to embodiments disclosed and described below can achieve this preferred separation scheme.

Figure 2:
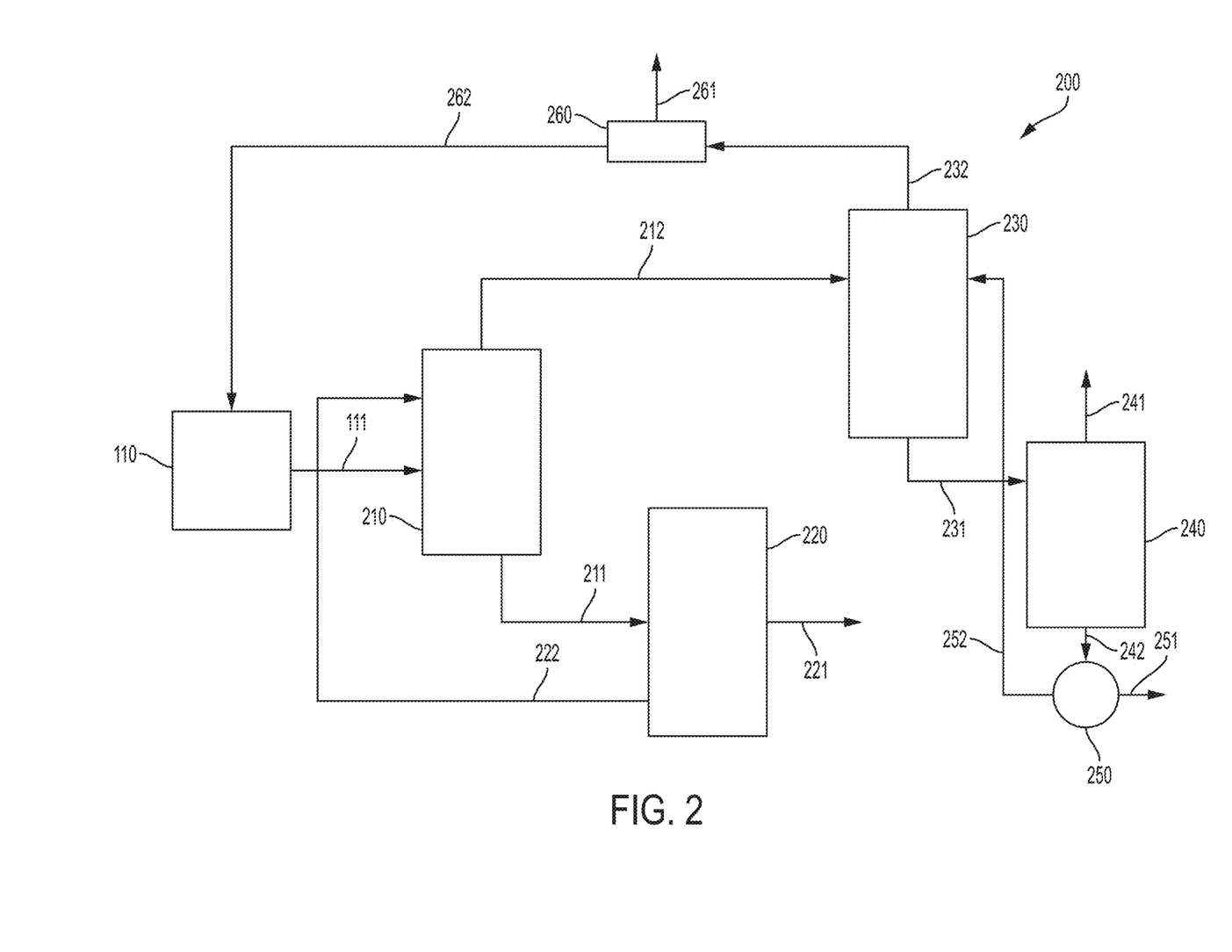
FIG. 2 schematically depicts a first system for separating $CO_2$ in the production of alkanes according to one or more embodiments disclosed and described herein.

With reference now to FIG. 2, systems and methods for separating $CO_2$ during alkane preparation using a two column distillation according to one or more embodiments is described. In the embodiments of $CO_2$ separation systems 200 shown in FIG. 2, a small amount of $CO_2$ (i.e., a purge amount of $CO_2$) is removed from the feed stream 111 in a $CO_2$ separator 210 before the process stream 212 comprising light alkanes is introduced into a first separation zone 230. However, unlike the conventional $CO_2$ separation systems described in reference to FIG. 1 above, in the $CO_2$ separation system 200 according to embodiments shown in FIG. 2, the process stream 212 that enters the first separation zone 230 comprises a significant amount of $CO_2$. In one or more embodiments, the process stream 212 comprises from 5 mass % to 40 mass % $CO_2$, such as from 10 mass % to 35 mass % $CO_2$, from 15 mass % to 30 mass % $CO_2$, or from 20 mass % to 25 mass % $CO_2$. In the embodiments of $CO_2$ separation systems depicted in FIG. 2, $CO_2$ is primarily separated from the light alkanes, including ethane, in the first separation zone 230 using a hydrocarbon solvent.

Details of the $CO_2$ separation systems 200 and methods according to embodiments depicted in FIG. 2 are described below.

In one or more embodiments, the $CO_2$ separation system 200 comprises a reaction zone 110 that is the same as the reaction zone 110 described above in reference to the conventional $CO_2$ separation systems as discussed above. A feed stream 111 that comprises light alkanes, $CO_2$ and one or more of $H_2$, CO, and $CH_4$ is sent from the reaction zone 110 to a $CO_2$ separator 210 that is fluidly connected to the reaction zone 110 and a $CO_2$ stripper 220. According to embodiments, in the $CO_2$ separator 210, the feed stream 111 is mixed with an amine solvent, such as, for example MEA, DEA, MDEA, or mixtures thereof, that isolates a small amount of $CO_2$ from the remaining components of the feed stream 111, such as, for example, light alkanes, CO, $H_2$, and $CH_4$. The amount of amine solvent and reaction conditions in the $CO_2$ separator 210 are selected, in various embodiments, such that only a small amount of $CO_2$ is isolated in the $CO_2$ separator 210.

The amount of $CO_2$ that is isolated by the amine solvent is, in one or more embodiments, an amount of $CO_2$ that is desired to be purged from the $CO_2$ separation system 200. The desired amount of $CO_2$ that is desired to be purged from the $CO_2$ separation system 200 is, in some embodiments, based on the amount of $CO_2$ that is to be recycled back to the reaction zone 110. Although not limited to any particular theory, the amount of $CO_2$ co-produced with light alkanes in the reaction zone 110 may depend on the combination of reactors and processes used in the reaction zone 110. It should be understood that it may also depend on the $H_2$:CO molar ratio used in the synthesis of light alkanes in reaction zone 110. In one or more embodiments, the molar $H_2$:CO ratio is from 1:1 to 10:1 such as from 7:1 to 9:1, or about 8:1. In some embodiments, the molar $H_2$:CO ratio is from 3:1 to 5:1, or about 3:1. In embodiments, a $CO_2$ solvent stream 211 comprising the purge amount of $CO_2$ and the amine solvent exits the $CO_2$ separator 210 and is sent to the $CO_2$ stripper 220. At the $CO_2$ stripper 220, the $CO_2$ in the $CO_2$ solvent stream 211 is extracted from the amine solvent and purged from the $CO_2$ separation system 200 as $CO_2$ purge 221. In various embodiments, after the $CO_2$ has been extracted from the $CO_2$ solvent stream 211, the amine solvent is sent from the $CO_2$ stripper 220 to the $CO_2$ separator 210 as solvent stream 222. It should be understood that in one or more embodiments, the $CO_2$ stripper 220 is any conventional extractor that is capable of extracting $CO_2$ from an amine solvent.

As discussed above, according to one or more embodiments, a process stream 212 that comprises light alkanes, $CO_2$, and one or more of CO, $H_2$, and $CH_4$ is sent from the $CO_2$ separator 210 to the first separation zone 230. The first separation zone 230 is fluidly connected to the $CO_2$ separator 210, the reaction zone 110, and a second separation zone 240. In the first separation zone 230, according to various embodiments, the light alkanes in the process stream 212 are separated from $CO_2$ and one or more of CO, $H_2$, and $CH_4$ that are present in the process stream 212. In some embodiments, this separation may be conducted by any suitable process. However, in one or more embodiments, the first separation zone 230 is a combined demethanizer/extractive distillation column that separates light alkanes from $CO_2$ and one or more of CO, $H_2$, and $CH_4$. In one or more embodiments, the separation zone 230 comprises a hydrocarbon solvent for separating the light alkanes from $CO_2$ and one or more of CO, $H_2$, and $CH_4$. In embodiments, the hydrocarbon solvent may be $C_3$ to $C_5$ alkanes that are recycled from the second separator 240 as described in more detail below. A light alkane stream 231 that comprises $C_2$ to $C_5$ alkanes exits the first separation zone 230 and is sent to the second separation zone 240. A recycle stream 232 comprising $CO_2$ and one or more of CO, $H_2$, and $CH_4$ exits the first separation zone 230 and is sent back to the reaction zone 110.

In some embodiments, the recycle stream 232 may comprise inert gases, such as, for example, nitrogen or argon, which, in some embodiments, may be present in the feed stream 111. In such embodiments, an optional first splitter 260 may be fluidly connected to the first separation zone 230 and the reaction zone 110 such that the recycle stream 232 passes through the first splitter 260. At the first splitter 260, a portion of the recycle stream 232 is removed from the $CO_2$ separation system 200 as an inert gas containing stream 261. The remainder of the recycle stream 232 exits the first splitter 260 as a second recycle stream 262 and is sent to the reaction zone 110. In embodiments, a portion of the recycle stream 232 is withdrawn from the process to prevent inert build-up and the remaining portion of stream 232 is sent directly from the first separation zone 230 to the reaction zone 110 as the second recycle stream 262. In one or more embodiments, the recycle stream 232, the inert gas containing stream 261, and the second recycle stream 262 have the same composition. It should be understood that any conventional device that can separate gas stream 232 into two streams and regulate the flow of gaseous stream 232 in each of the two streams may be used as the first splitter 260.

As discussed above, in embodiments, a light alkane stream 231 exits the first separation zone 230 and is sent to the second separation zone 240. The second separation zone 240 is, in embodiments, fluidly connected to the first separation zone 230 and a second splitter 250. In the second separation zone 240, the light alkanes are separated into a first product stream 241 comprising $C_2$ alkanes and a second product stream 242 that comprises $C_3$ to $C_5$ alkanes. In some embodiments, the first product stream 241 comprises from 10 mass % to 90 mass % $C_2$ alkanes, such as from 20 mass % to 80 mass % $C_2$ alkanes, from 30 mass % to 70 mass % $C_2$ alkanes, or from 30 mass % to 60 mass % $C_2$ alkanes. In one or more embodiments, the first product stream 241 consists essentially of $C_2$ to $C_3$ alkanes. This separation of the light alkanes into the first product stream 241 that comprises $C_2$ alkanes and the second product stream 242 that comprises $C_3$ to $C_5$ alkanes may, in various embodiments, be completed by any known separation method, such as, for example distillation. In one or more embodiments, the second product stream 242 comprises from 30 mass % to 95 mass % $C_3$ to $C_5$ alkanes, such as from 40 mass % to 90 mass % $C_3$ to $C_5$ alkanes, from 50 mass % to 90 mass % $C_3$ to $C_5$ alkanes, or from 60 mass % to 85 mass % $C_3$ to $C_5$ alkanes. The first product stream 241 exits the $CO_2$ separation system 200 and can be used as products or starting materials in other chemical processing. In some embodiments, the second product stream 242 exits the second separation zone 240 and is sent to the second splitter 250 that is fluidly connected to the second separation zone 240 and the first separation zone 230.

According to one or more embodiments, the second product stream 242 is split at the second splitter 250 into a third product stream 251 and a hydrocarbon solvent stream 252. In embodiments, the second product stream 242 is physically split into the third product stream 251 and the hydrocarbon solvent stream 252 and, thus, the third product stream 251 has the same composition as the hydrocarbon solvent stream 252. In one or more embodiments, the third product stream 251 exits the $CO_2$ separation system 200 and can be used as products or starting materials in other chemical processing. The hydrocarbon solvent stream 252, which comprises $C_3$ to $C_5$ alkanes, is sent back to the first separation zone 230, where, in one or more embodiments, it is used as a solvent to separate the process stream 212 into the recycle stream 232—that comprises $CO_2$ and one or more of CO, $H_2$, and $CH_4$—and light alkane stream 231. It should be understood that, in embodiments, any splitter capable of separating the second product stream 242 into two streams may be used as the second splitter 250.

As discussed above, in some embodiments, the hydrocarbon solvent stream 252 exits the second splitter 250 and is sent to the first separation zone 230 where it is used as a solvent to separate process stream 212 into light alkane stream 231 and recycle stream 232. In embodiments, the amount of hydrocarbon solvent 252 that is directed to the first separation zone 230 is an amount such that the weight ratio of hydrocarbon solvent in the first separation zone 230 to the light alkanes in the first separation zone 230 is from 1:1 to 5:1, such as from 1:1 to 3:1, or from 2:1 to 3:1.

Figure 3:
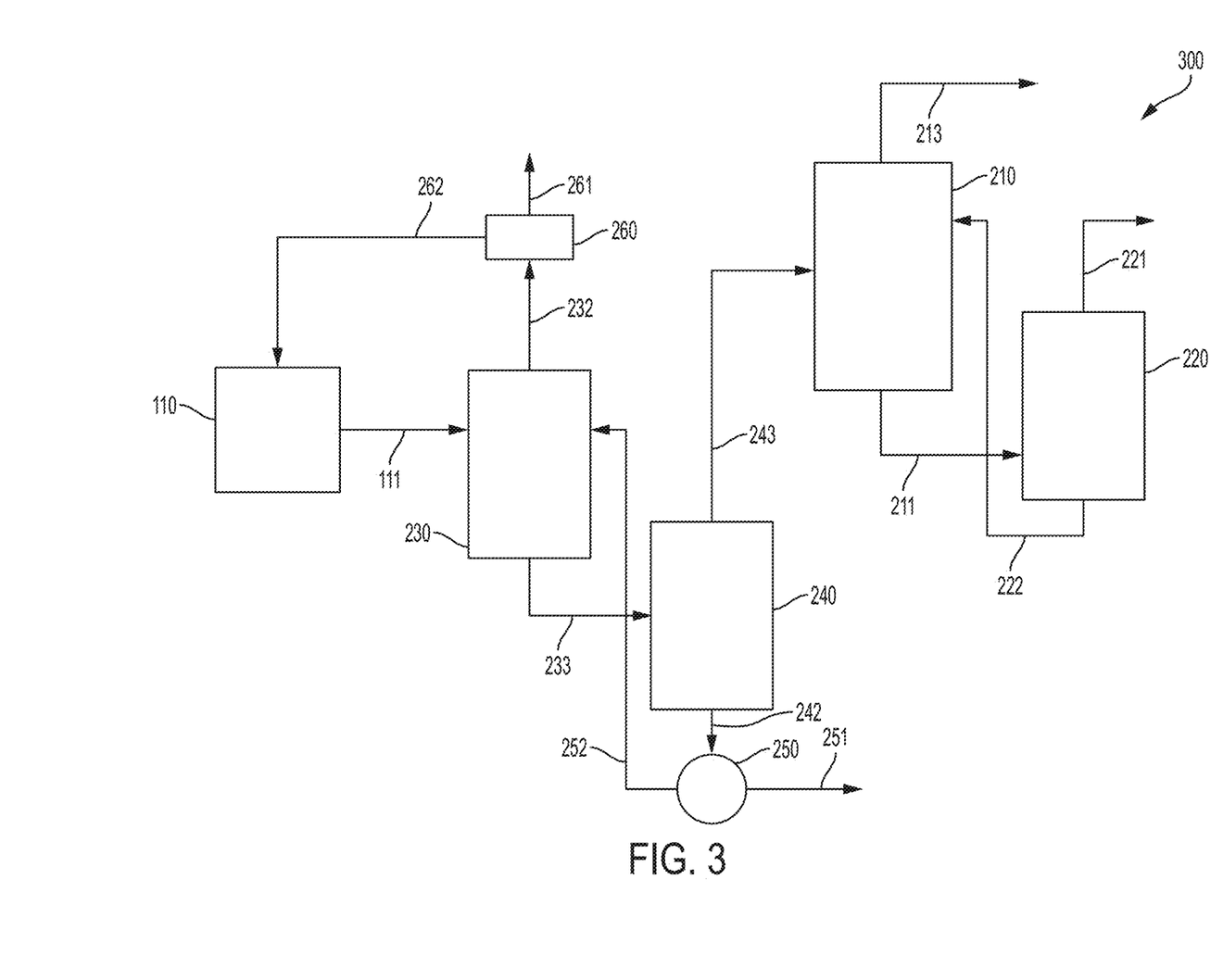
FIG. 3 schematically depicts a second system for separating $CO_2$ in the production of alkanes according to one or more embodiments disclosed and described herein.

With reference now to FIG. 3, further embodiments of systems and methods for separating $CO_2$ during alkane preparation using a two column distillation are described. In the embodiments of $CO_2$ separation systems 300 shown in FIG. 3, the feed stream 111 is fed directly to the first separation zone 230 without removing any $CO_2$ from the feed stream 111. Details of the $CO_2$ separation systems 300 and methods according to embodiments depicted in FIG. 3 are described below.

In one or more embodiments, the $CO_2$ separation system 300 comprises a reaction zone 110 that is the same as the reaction zone 110 described above in reference to the conventional $CO_2$ separation systems depicted in FIG. 1 and the $CO_2$ separation systems depicted in FIG. 2. In some embodiments, a feed stream 111 that comprises light alkanes, $CO_2$ and one or more of $H_2$, CO, and $CH_4$ is sent from the reaction zone 110 to a first separation zone 230. The first separation zone 230 is fluidly connected to the reaction zone 110 and a second separation zone 240. In the first separation zone 230, according to various embodiments, the light alkanes in the feed stream 111 are separated from the $CO_2$ and one or more of CO, $H_2$, and $CH_4$ that are present in the feed stream 111. In embodiments, this separation may be conducted by any suitable process. However, in one or more embodiments, the first separation zone 230 is a combined demethanizer/extractive distillation column that separates light alkanes from $CO_2$ and one or more of CO, $H_2$, and $CH_4$. In some embodiments, the first separation zone 230 comprises a hydrocarbon solvent for separating the light alkanes from $CO_2$ and one or more of CO, $H_2$, and $CH_4$. In embodiments, the hydrocarbon solvent may be $C_3$ to $C_5$ alkanes that are recycled from the second separation zone 240 as described in more detail below. In various embodiments, a second process stream 233 that comprises $C_2$ to $C_5$ alkanes and a small amount of $CO_2$ exits the first separation zone 230 and is sent to the second separation zone 240. A recycle stream 232 comprising $CO_2$ and one or more of CO, $H_2$, and $CH_4$ exits the first separation zone 230 and is sent back to the reaction zone 110.

In some embodiments, the recycle stream 232 may comprise inert gases, such as, for example, nitrogen or argon, which may be introduced by the feed stream 111. In such embodiments, an optional first splitter 260 may be fluidly connected to the first separation zone 230 and the reaction zone 110 such that the recycle stream 232 passes through the first splitter 260. At the first splitter 260, a portion of the recycle stream 232 is removed from the $CO_2$ separation system 300 as an inert gas containing stream 261. The remainder of the recycle stream 232 exits the first splitter 260 as a second recycle stream 262 and is sent to the reaction zone 110. In embodiments, a portion of the recycle stream 232 is withdrawn from the process to prevent inert build-up and the remaining portion of the recycle stream 232 is sent directly from the first separation zone 230 to the reaction zone 110 as the second recycle stream 262. In one or more embodiments, the recycle stream 232, the inert gas containing stream 261, and the second recycle stream 262 have the same composition. It should be understood that any conventional device that can separate the recycle stream 232 into two streams and regulate the flow of the recycle stream 232 in each of the two streams may be used as the first splitter 260.

As stated above, in embodiments, a second process stream 233 exits the first separation zone 230 and is sent to the second separation zone 240. The second separation zone 240 is, in embodiments, fluidly connected to the first separation zone 230 and a second splitter 250. In the second separation zone 240, the light alkanes in the second process stream 233 are separated into a third process stream 243—that comprises $C_2$ alkanes and a small amount of $CO_2$ (i.e., a purge amount of $CO_2$)—and a second product stream 242 that comprises $C_3$ to $C_5$ alkanes. This separation of the light alkanes into the third process stream 243 and the second product stream 242 may, in various embodiments, be completed by any known separation method, such as, for example distillation. The third process stream 243 exits the second separation zone 240 and is sent to the $CO_2$ separator 210. The second product stream 242 exits the second separation zone 240 and is sent to the second splitter 250 that is fluidly connected to the second separation zone 240 and the first separation zone 230.

According to embodiments, at the second splitter 250 the second product stream 242 is split into a third product stream 251 and a hydrocarbon solvent stream 252. In one or more embodiments, the second product stream 242 comprises from 30 mass % to 95 mass % $C_3$ to $C_5$ alkanes, such as from 40 mass % to 90 mass % $C_3$ to $C_5$ alkanes, from 50 mass % to 90 mass $C_3$ to $C_5$ alkanes, or from 60 mass % to 85 mass % $C_3$ to $C_5$ alkanes. In embodiments, the second product stream 242 is physically split into the third product stream 251 and the hydrocarbon solvent stream 252 and, thus, the third product stream 251 has the same composition as the hydrocarbon solvent stream 252. The third product stream 251 exits the $CO_2$ separation system 300 and can be used as products or starting materials in other chemical processing. The hydrocarbon solvent stream 252, which comprises $C_3$ to $C_5$ alkanes, is sent back to the first separation zone 230, where, in one or more embodiments, it is used as a hydrocarbon solvent to separate the feed stream 111 into the recycle stream 232—that comprises $CO_2$ and one or more of CO, $H_2$, and $CH_4$—and second process stream 233. It should be understood that, in embodiments, any splitter capable of separating the second product stream 242 into two streams may be used as the second splitter 250.

As discussed above, in some embodiments, the hydrocarbon solvent stream 252 exits the second splitter 250 and is sent to the first separation zone 230 where it is used as a solvent to separate feed stream 111 into the second process stream 233 and recycle stream 232. In embodiments, the amount of hydrocarbon solvent 252 that is directed to the first separation zone 230 is an amount so that the weight ratio of hydrocarbon solvent in the first separation zone 230 to the amount of light alkanes in the first separation zone 230 is from 1:1 to 5:1, such as from 1:1 to 3:1, or from 2:1 to 3:1.

As discussed above, in one or more embodiments, the third process stream 243 exits the second separation zone 240 and is sent to the $CO_2$ separator 210 that is fluidly connected to the second separation zone 240 and a $CO_2$ stripper 220. In one or more embodiments, the third process stream 243 comprises from 5 mass % to 40 mass % $CO_2$, such as from 10 mass % to 35 mass $CO_2$, from 15 mass % to 30 mass % $CO_2$, or from 20 mass % to 25 mass % $CO_2$. According to embodiments, in the $CO_2$ separator 210, the third process stream 243 is mixed with an amine solvent, such as, for example MEA, DEA, MDEA, or mixtures thereof, that isolates the small amount of $CO_2$ (i.e., the purge amount of $CO_2$) remaining in the third process stream 243. The amount of amine solvent and reaction conditions in the $CO_2$ separator 210 are selected, in various embodiments, such that only the small amount of $CO_2$ is isolated in the $CO_2$ separator 210. As described above, the desired amount of $CO_2$ that is to be purged from the $CO_2$ separation system 300 is, in some embodiments, based upon the amount of $CO_2$ that is to be recycled back to the reaction zone 110. Namely, in embodiments, the amount of $CO_2$ that is to be recycled back to the reaction zone 110 is included in recycle stream 232. Thus, any difference between the amount of $CO_2$ in the feed stream 111 and the desired amount that is included in the recycle stream 232 is sent to the $CO_2$ separator 210 to be isolated by the amine solution and ultimately purged from the $CO_2$ separation system.

In embodiments, a $CO_2$ solvent stream 211 comprising the purge amount of $CO_2$ and the amine solvent exits the $CO_2$ separator 210 and is sent to the $CO_2$ stripper 220. At the $CO_2$ stripper 220, the $CO_2$ in the $CO_2$ solvent stream 211 is stripped from the amine solvent and purged from the $CO_2$ separation system 300 as $CO_2$ purge 221. In various embodiments, after the $CO_2$ has been stripped from the $CO_2$ solvent stream 211, the amine solvent is sent from the $CO_2$ stripper 220 to the $CO_2$ separator 210 as solvent stream 222. It should be understood that in one or more embodiments, the $CO_2$ stripper 220 is any conventional stripper that is capable of stripping $CO_2$ from an amine solvent.

According to one or more embodiments, a fourth product stream 213 that comprises $C_2$ alkanes exits the $CO_2$ separator 210 and the $CO_2$ separation system 300 where it can be used as a product or starting materials for various chemical processes. In some embodiments, the fourth product stream 213 comprises from 10 mass % to 90 mass % $C_2$ alkanes, such as from 20 mass to 80 mass % $C_2$ alkanes, from 30 mass % to 70 mass % $C_2$ alkanes, or from 30 mass % to 60 mass % $C_2$ alkanes. In one or more embodiments, the fourth product stream 213 consists essentially of $C_2$ to $C_3$ alkanes.

The systems and method for separating $CO_2$ in the preparation of alkanes according to embodiments disclosed and described herein reduce the energy required to separate $CO_2$ from the alkane-containing product stream. Because only a small amount of $CO_2$ is absorbed into the solvent to isolate the $CO_2$ from the light alkanes, only a small fraction of the energy required in conventional $CO_2$ separation systems. Further, the recycle stream, which comprises $CO_2$, described in embodiments herein is pressurized, thus no, or very little,compression of the recycle stream is required before it is introduced into the reaction zone 110.

EXAMPLES

Embodiments will be further clarified by the following examples, which were simulated using Aspen simulation software.

Example 1

A gas feed containing $H_2$, $CH_4$, CO, $CO_2$, ethane, propane, butane, and pentane was separated into three streams using two columns. A portion of $CO_2$, which must be removed from the system, was separated before a first separation zone. For this example, the $CO_2$ purge rate was 16,400 kg/hr. The first column was a distillation column with a solvent feed on the top tray. The overhead gas stream product for recycle back to the reactor contained $H_2$, CO, $CO_2$, and $CH_4$. The remaining products were separated into two streams by distillation. The overhead product stream contained $C_2$ and some $C_3$. A portion of the tails stream was used as the solvent to the first column, and the remainder was the tails product containing $C_3$, $C_4$, and $C_5$. The specifics of the distillation columns are provided in Table 1:

TABLE 1

| Column 1 (Extractive Distillation) | |
|---|---|
| Number of Trays | 52 |
| Feed Tray | 35 |
| Solvent Feed Tray | 1 |
| Column 2 | |
| Number of Trays | 35 |
| Feed Tray | 10 |

The reflux rates and heat loads on column 1 and column 2 are provided in Table 2:

TABLE 2

| Column 1 | |
|---|---|
| Reflux Rate | 186,284 kg/hr |
| $Q_{condenser1}$ | −32.6 MMBtu/hr |
| $Q_{reboiler1}$ | 46.7 MMBtu/hr |
| Column 2 | |
| Reflux Rate | 80,000 kg/hr |
| $Q_{condenser2}$ | −28.4 MMBtu/hr |
| $Q_{reboiler2}$ | 27.0 MMBtu/hr |

Table 3 below provides mass balance for all the streams of Example 1. The streams described in Table 3 are as follows: D1 is the overhead flow from column 1; B1 is the bottoms flow from column 1 and the feed to column 2; D2 is the overhead flow from column 2; B2 is the bottoms flow from column 2; B2 product is the portion of B2 taken out as product; B2 recycle is the solvent feed to column 1. The total alkane production rate was about 36,600 kg/hr.

TABLE 3

Mass Balance for all Streams for Example 1

| | Gas Feed | Solvent Feed (B2 recycle) | D1 | B1 | D2 | B2 | B2 product |
|---|---|---|---|---|---|---|---|
| Temp, °C. | 30.9 | −11.4 | −39.6 | 98.6 | 31.6 | 109.8 | 109.8 |
| P, $bar_g$ | 33.5 | 33.5 | 33.5 | 33.5 | 27.6 | 27.6 | 27.6 |
| flow, kg/hr | 114,359 | 100,000 | 77,773 | 136,586 | 23,658 | 112,927 | 12,927 |
| Total Flow kmol/hr | 5692 | 1854 | 4807 | 2739 | 645 | 2094 | 240 |
| Composition in mole fraction | | | | | | | |
| $H_2$ | 0.4568 | 0.0000 | 0.5408 | 0.0000 | 0.0000 | 0.0000 | 0.0000 |
| CO | 0.0469 | 0.0000 | 0.0555 | 0.0000 | 0.0000 | 0.0000 | 0.0000 |
| $CO_2$ | 0.1964 | 0.0000 | 0.2312 | 0.0024 | 0.0104 | 0.0000 | 0.0000 |
| $CH_4$ | 0.1275 | 0.0000 | 0.1510 | 0.0000 | 0.0000 | 0.0000 | 0.0000 |
| $C_2H_6$ | 0.0630 | 0.0018 | 0.0032 | 0.1265 | 0.5311 | 0.0018 | 0.0018 |
| $C_3H_8$ | 0.0842 | 0.4531 | 0.0158 | 0.4539 | 0.4564 | 0.4531 | 0.4531 |
| $C_4H_{10-01}$ | 0.0184 | 0.3866 | 0.0022 | 0.2960 | 0.0021 | 0.3866 | 0.3866 |
| $C_5H_{12-01}$ | 0.0068 | 0.1585 | 0.0002 | 0.1212 | 0.0000 | 0.1585 | 0.1585 |

The energy requirement for the separation can be calculated on a fuel gas equivalent basis. For this comparison, energy for steam and electrical generation must be put on a consistent basis. The efficiency for converting fuel gas to steam is selected to be at 85%. The cooling requirement must be converted to the electrical power needed to perform the cooling, which depends on the cooling temperature. A relationship between cooling temperature and electrical power is taken from Hall, "Rules of Thumb for Chemical Engineers", p. 194, Chapter 11. Selected values are given in Table 4 below.

TABLE 4

| T, °C. | HP/Ton Refrigeration |
|---|---|
| −17.8 | 1.75 |
| −40.0 | 3.01 |
| −51.1 | 3.79 |
| −73.3 | 5.69 |
| −95.6 | 8.18 |

In addition, the electrical power must be converted to a fuel gas equivalent. For this analysis, the efficiency for converting fuel gas to electrical energy is selected as 34%.

Energy Requirement

| Cooling Temp, °C. | Cooling Duty MMBtu/hr | Power Requirement kw/(MMBtu/hr) | Fuel Gas Equivalent, MMBtu/yr |
|---|---|---|---|
| −39.6 C. | −32.6 | 187 | 61 |

For CO2 removal, the energy requirement basis is assumed to be 2 GJ/ton $CO_2$, or 860 Btu/lb. This is taken from Straelen, and Geuzebroek, "The Thermodynamic minimum regeneration energy required for post-combustion $CO_2$ capture", ScienceDirect, 2010. The energy breakdown in terms of fuel gas equivalent in given in Table 5 below.

TABLE 5

| | Fuel Gas Equivalent Energy in MMBtu/hr |
|---|---|
| Refrigeration | 61 |
| $CO_2$ Removal | 31 |
| Reboiler 1 | 54 |
| Reboiler 2 | 32 |
| Total Energy | 178 |
| Unit Energy, Btu/lb alkane | 2240 Btu/lb alkane product |

Example 2

In this example, the portion of $CO_2$ that was removed from the reaction loop was included in the feed to the first distillation column. This $CO_2$ leaves the first column in the tails with the other $C_{2+}$ alkane components, and ends up in the second column product.

The reflux rates and heat loads on column 1 and column 2 are provided in Table 6:

TABLE 6

| Column 1 | |
|---|---|
| Reflux Rate | 177,294 kg/hr |
| $Q_{condenser1}$ | −29.7 MMBtu/hr |
| $Q_{reboiler1}$ | 27.8 MMBtu/hr |
| Column 2 | |
| Reflux Rate | 42,000 kg/hr |
| $Q_{condenser2}$ | −23.0 MMBtu/hr |
| $Q_{reboiler2}$ | 31.8 MMBtu/hr |

The mass balance for all streams is given in Table 7. The streams in Table 7 have the same designations as the streams in Table 3 of Example 1.

TABLE 7

Mass Balance for all Streams for Example 2

| | Gas Feed | Solvent Feed | D1 | B1 | D2 | B2 | B2 product |
|---|---|---|---|---|---|---|---|
| Temp, ° C. | 30.5 | −10.5 | −38.0 | 64.0 | 0.6 | 109.1 | 109.1 |
| P, bar$_g$ | 33.5 | 33.5 | 33.5 | 33.5 | 27.6 | 27.6 | 27.6 |
| flow, kg/hr | 131,236 | 100,000 | 78,534 | 152,703 | 39,604 | 113,082 | 13,082 |
| Total Flow kmol/hr | 6075 | 1860 | 4824 | 3111 | 1008 | 2103 | 243 |
| mole fraction | | | | | | | |
| $H_2$ | 0.4280 | 0.0000 | 0.5390 | 0.0000 | 0.0000 | 0.0000 | 0.0000 |
| CO | 0.0439 | 0.0000 | 0.0553 | 0.0000 | 0.0000 | 0.0000 | 0.0000 |
| $CO_2$ | 0.2454 | 0.0000 | 0.2318 | 0.1198 | 0.3696 | 0.0000 | 0.0000 |
| $CH_4$ | 0.1195 | 0.0000 | 0.1504 | 0.0002 | 0.0005 | 0.0000 | 0.0000 |
| $C_2H_6$ | 0.0590 | 0.0018 | 0.0032 | 0.1113 | 0.3400 | 0.0018 | 0.0018 |
| $C_3H_8$ | 0.0803 | 0.4629 | 0.0176 | 0.4063 | 0.2882 | 0.4629 | 0.4629 |
| $C_4H_{10\text{-}01}$ | 0.0174 | 0.3791 | 0.0024 | 0.2568 | 0.0017 | 0.3791 | 0.3791 |
| $C_5H_{12\text{-}01}$ | 0.0064 | 0.1562 | 0.0002 | 0.1056 | 0.0000 | 0.1562 | 0.1562 |

Table 8 below provides the energy requirements for Example 2, which were calculated in the same manner as provided above in Example 1.

TABLE 8

| Cooling Temp, C. | Cooling Duty MMBtu/hr | Power Requirement kw/(MMBtu/hr) | Fuel Gas Equivalent, MMBtu/yr |
|---|---|---|---|
| −38 C. | −29.7 | 180 | 54 |
| 0. | −22.9 | 62 | 14 |

For $CO_2$ removal, the energy requirement basis is assumed to be 860 Btu/lb $CO_2$. The energy breakdown in terms of fuel gas equivalent in given in Table 9 below.

TABLE 9

| | Fuel Gas Equivalent Energy in MMBtu/hr |
|---|---|
| Refrigeration | 68 |
| $CO_2$ Removal | 31 |

TABLE 9-continued

| | Fuel Gas Equivalent Energy in MMBtu/hr |
|---|---|
| Reboiler 1 | 33 |
| Reboiler 2 | 37 |
| Total Energy | 169 |
| Unit Energy, Btu/lb alkane | 2116 Btu/lb alkane product |

This case gives a slightly higher refrigeration cost due to the lower overhead temperature of column D2, but reduced reboiler cost for the first column. The net result is slightly lower energy cost/lb alkane product.

Comparative Example

In this Comparative Example, a conventional separation system, such as the system shown in FIG. 1 was used. For this Comparative Example, all $CO_2$, (i.e., 65,600 kg/hr), was removed from the feed gas. A portion of the $CO_2$, 16,400 kg/hr, was purged from the process, and the remainder was compressed and recycled back to the reactor. The remaining gas stream after the $CO_2$ removal was cooled in steps to −100° C. The condensed liquid was fed to a demethanizer distillation column, which separated the $C_{2+}$ alkanes in the tails, and the overhead contained $CH_4$, CO, and some $H_2$. The design specifications on the column were 0.0001 mass purity $CH_4$ in the tails and 0.005 mass purity ethane in the overhead, which were met by controlling the reflux ratio and the distillate to feed (D/F) ratio.

The uncondensed gas feed contained mostly $H_2$ (73%), $CH_4$ (18%), CO (7.3%), and $C_2H_6$ (1.9%). The ethane concentration was reduced further by expanding this stream through a turboexpander for cooling, and feeding the condensed product back to the column. The cold gas stream was used to cool the feed. The gas stream, containing Hz, $CH_4$, and CO was compressed back to reactor pressure for recycle, and the overall recycle composition was the same as in Example 1.

Results of the energy balance are given below in Table 10 below:

TABLE 10

|  | Fuel Gas Equivalent Energy in MMBtu/hr |
| --- | --- |
| Refrigeration | 38 |
| $CO_2$ Removal | 124 |
| $CO_2$ Compression | 42 |
| Recycle Gas Compression | 40 |
| Column Reboiler | 14 |
| Total Energy | 259 |
| Unit Energy, Btu/lb alkane | 3252 Btu/lb alkane product |

This Comparative Example shows the increased energy usage of about 53% used in a conventional $CO_2$ removal system compared to the $CO_2$ removal system of Example 1 and 45% more energy used in the conventional $CO_2$ removal system compared to the $CO_2$ removal system of Example 2. In addition, the conventional $CO_2$ removal system was required to be about 4 times bigger due to a 4 times higher $CO_2$ removal rate. This conventional approach also requires compression of both the recycled $CO_2$ and the recycled Hz-rich stream, which requires additional capital.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

The invention claimed is:

1. A system for separating $CO_2$ from $C_2$ to $C_5$ alkanes, comprising:
 a first separation zone comprising a hydrocarbon solvent and that is configured to separate a first stream comprising $C_2$ to $C_5$ alkanes and $CO_2$ into a recycle stream and a second stream, wherein the recycle stream comprises $CO_2$ and one or more of CO, $H_2$, and $CH_4$, and the second stream comprises $C_2$ to $C_5$ alkanes;
 a second separation zone that is fluidly connected to the first separation zone and that is configured to separate the second stream into a third stream and a fourth stream, wherein the third stream comprises $C_2$ alkanes and the fourth stream comprises $C_3$ to $C_5$ alkanes; and
 a reaction zone that is fluidly connected to the first separation zone so that the recycle stream is introduced from the first separation zone to the reaction zone.

2. The system of claim 1, wherein the second separation zone is fluidly connected to the first separation zone so that a portion of the fourth stream is used as the hydrocarbon solvent in the first separation zone.

3. The system of claim 2, wherein the system further comprises a splitter that is fluidly connected to the second separation zone and the first separation zone so that the fourth stream is split into the hydrocarbon solvent and a product stream.

4. The system of claim 1, wherein the system further comprises a third separation zone comprising an amine solvent that is fluidly connected to one of the first separation zone or the second separation zone and that is configured to remove a purge amount of $CO_2$.

5. The system of claim 4, wherein the third separation zone is fluidly connected to the first separation zone.

6. The system of claim 4, wherein the third separation zone is fluidly connected to the second separation zone.

7. The system of claim 1, wherein the reaction zone is fluidly connected to the first separation zone so that the first stream is a feed stream introduced from the reaction zone to the first separation zone.

8. The system of claim 1, wherein the system further comprises a splitter that is fluidly connected to the first separation zone so that a portion of the recycle stream is purged at the splitter.

9. The system of claim 8, wherein the splitter is fluidly connected to the first separation zone and the reaction zone so that a portion of the recycle stream is introduced from the first separation zone to the reaction zone.

10. The system of claim 1, wherein the first separation zone is a combined demethanizer/extractive distillation column.

11. The system of claim 1, wherein the second separation zone comprises a distillation column.

12. The system of claim 1, wherein the first stream comprises from 5 mass % to 40 mass % $CO_2$.

* * * * *